United States Patent [19]
Hassenboehler

[11] 3,958,452
[45] May 25, 1976

[54] UNIFORM PLANAR STRAIN TESTER

[75] Inventor: Charles B. Hassenboehler, Metairie, La.

[73] Assignee: The United States of America as represented by the Secretary of Agriculture, Washington, D.C.

[22] Filed: Jan. 23, 1975

[21] Appl. No.: 543,705

[52] U.S. Cl. .................................. 73/95
[51] Int. Cl.² ............................ G01N 3/08
[58] Field of Search ............ 73/95, 102, 159

[56] References Cited
UNITED STATES PATENTS 3,807,224   4/1974   Hassenboehler ................. 73/95

*Primary Examiner*—James J. Gill
*Assistant Examiner*—Anthony J. Ciarlante
*Attorney, Agent, or Firm*—M. Howard Silverstein; Max D. Hensley; Salvador J. Cangemi

[57] ABSTRACT

This invention relates to an apparatus for stretching a textile material such that the magnitude of the strain at all points is equal in all directions in the plane of the specimen. The embodiment disclosed is an expandable circular pin frame. The pins mounted in puley are uniformly displaced radially outward and impart uniform radial strain without the edge effects associated with similar apparatus employing nonexpanding fastening mechanisms.

1 Claim, 4 Drawing Figures

UNIFORM PLANAR STRAIN TESTER

This invention relates to an apparatus whereby a colinear separation of two embodied plates can be caused to stretch a material to a constant state of strain at all points in the plane of the material.

A problem of long standing in textile testing instruments is that of producing uniform biaxial strain in a specimen by a simple means. In measuring the elastic properties of textiles, tensile testers having jaws of fixed dimensions to clamp the specimen produce edge effects when the specimen is stretched. Heretofore, techniques for biaxial stretching require large and elaborate samples to eliminate edge effects. Simple apparatuses such as the Mullen diaphragm tester (Federal Test Method 191, Dec. 31, 1968; Method 1522) and the Celanese bagging tester (Thomas, Walter, Jr.) Celanese Bagging Test for Knit Fabrics, Text. Chem. Color. 3, 231–233 (1971)), do not produce nor attempt to produce uniform ratio of planar strain over the test surface of the specimen. In the Mullen and Celanese tests, the perimeter of a circular specimen is held fixed by nonexpanding clamps while the interior of the specimen is deformed by an inflatable membrane or by a sphere pushed against the center of the specimen. The resultant strain, at any point in the specimen, is some function of the radial and angular orientation of the point in the plane of the specimen.

A main object of this invention is to provide a machine to impart stretch to a textile specimen of a general nature such that the ratio of the biaxial strain remains constant and the state of strain at a point for a given stretch level is constant at any point in the plane of the specimen.

Another object of this invention is to provide an apparatus producing stretch of this nature, one embodiment of which includes an expandable circular pin frame "jaw", composed of rotatable pinned pulleys situated in the form of a torus, without the edge effects associated with similar apparatuses employing nonexpanding jaws.

Another object of this invention is to provide means for prestraining a textile specimen prior to subjecting it to further stretching of the nature generalized above.

A further object of this invention is to provide a testing instrument producing strain of this generalized nature for which the deformation, elastic recovery, and the force required to produce this said strain can be measured accurately.

Still another object of this invention is to simply the means for mesuring the elastic recovery response of textiles stretched under a uniform state of planar strain recovering under a given value of residual stretching force.

A still further object of this invention is to stretch knitted fabrics such that yarn loop sliding is minimized in order that effects of certain constituent yarn properties can be evaluated.

In particular, this invention relates to a biaxial strain tester in which conventional fixed jaw edge effects and the tendency to neck while straining the textile specimen are eliminated.

More particularly, this invention relates to a strain tester, one embodiment of which produces biaxial strain in the plane of the specimen at a strain ratio of unity, capable of producing strain in a textile specimen similar to the strain encountered in the textile covering the jointed parts of the human body during flexing motions.

These and additional objects and advantages of this invention will be apparent from the following drawings, specifications, and claims set forth herein.

The uniform strain tester, according to the instant invention, is described in detail below, reference being made to the accompanying drawings in which.

Figure 1A:
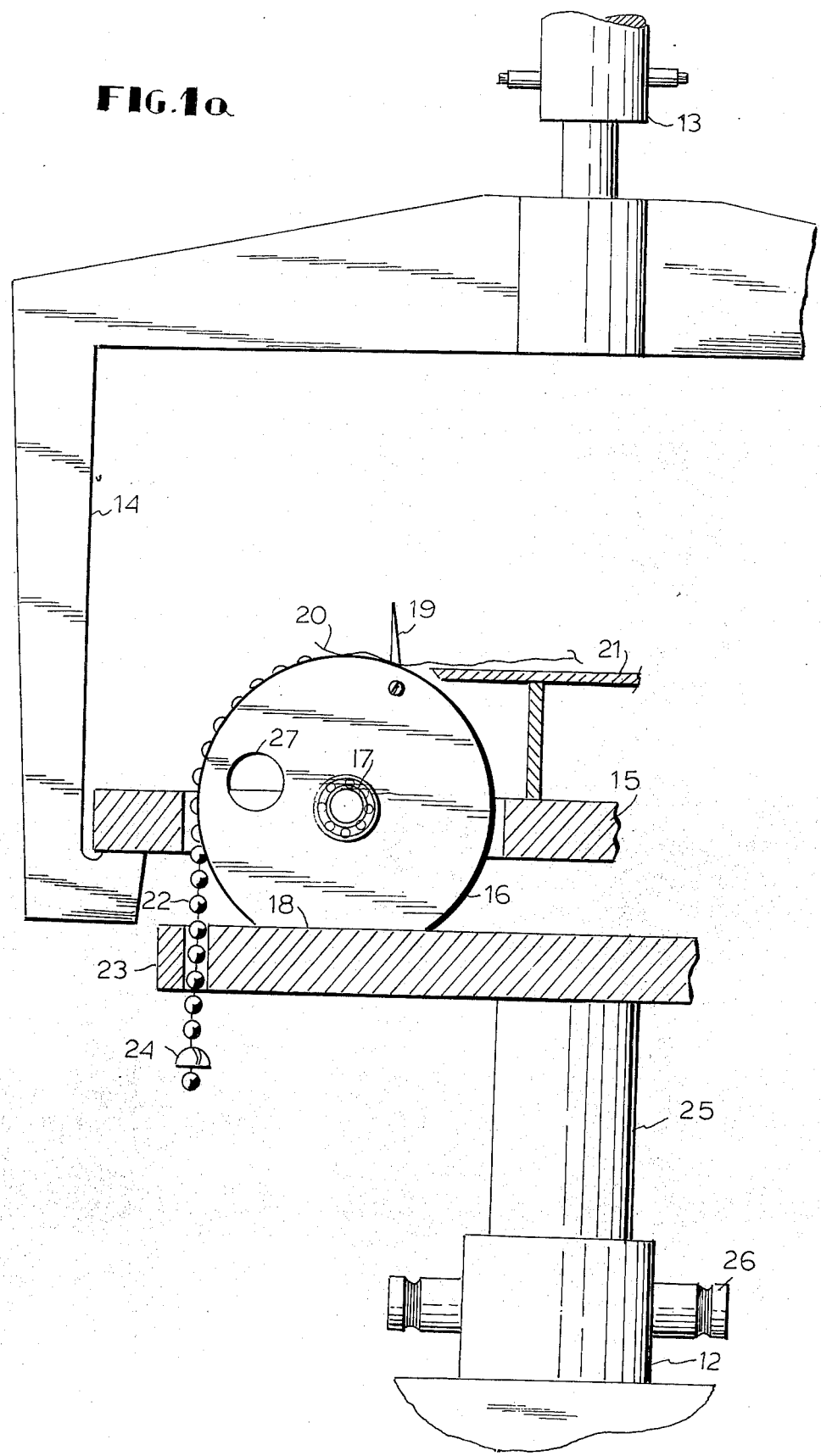
FIG. 1a represents a partial cross-sectional view of one angular unit of an embodiment showing a pulley partially in full view and partially in cross section.

Referring to the drawings, FIG. 1a is a schematic showing an angular unit used in an embodiment producing constant radial stretch described below.

Uniform planar strain tester assembly is installed in crosshead receiver 12 and load cell coupling 13 of a conventional tensile testing machine not shown in which the crosshead is capable of up and down colinear movement.

Yoke 14, joins pulley plate 15 to the load cell coupling 13 of the tensile testing machine (not shown).

Pulley plate 15 has pulleys 16 positioned equiangularly and equidistant from the center of the plate 15 and having the central plane of the pulleys 16 perpendicular to and containing a radius of the plate 15. Pulleys 16 revolve on press-in low-friction bearings 17 pressed into bearing shafts that fit into kerfs not shown in plate 15 and held in place with bolted on plates. Pulleys 16 have a chordal flat 18 perpendicular to needle 19 said flat integral pulley 16.

A specimen 20 is mounted onto needles 19 and rests on a disk-shaped specimen support plate 21, integral plate 15. Beat chains 22 are adjustably fastened to pulleys 16 at a point adjacent to needle 19 and hang through matching aligned holes in base plate 23 of diameter sufficient to pass bead chains with clearance. Modified bead-chain clips 24 adjustably define minimum separation of plates 15 and 23 at which a pulley 16 is rotated. Flange 25 fits into crosshead receiver 12 and is held in place by pin 26. Hole 27 balances the torque due to the chain overhand. At the minimum plate separation, FIG. 1a, the chordal flats lie on a plane surface thus providing a stable support for rigidly orienting needles 19 perpendicular to plate 15 during specimen mounting procedures.

Figure 1C:
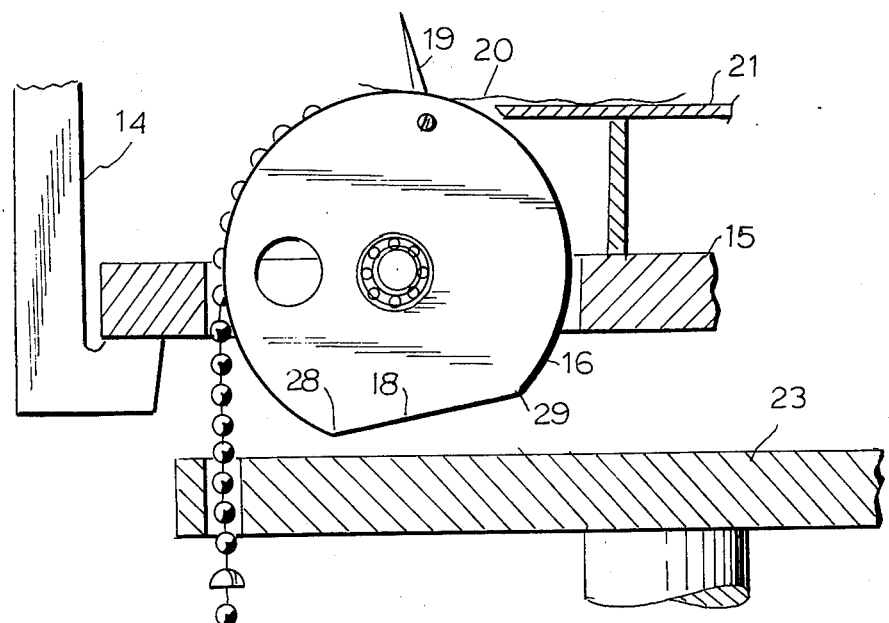
FIG. 1c is a partial cross-sectional view showing impending indexing action following a test as the horizontal plates approach each other.
Figure 1B:
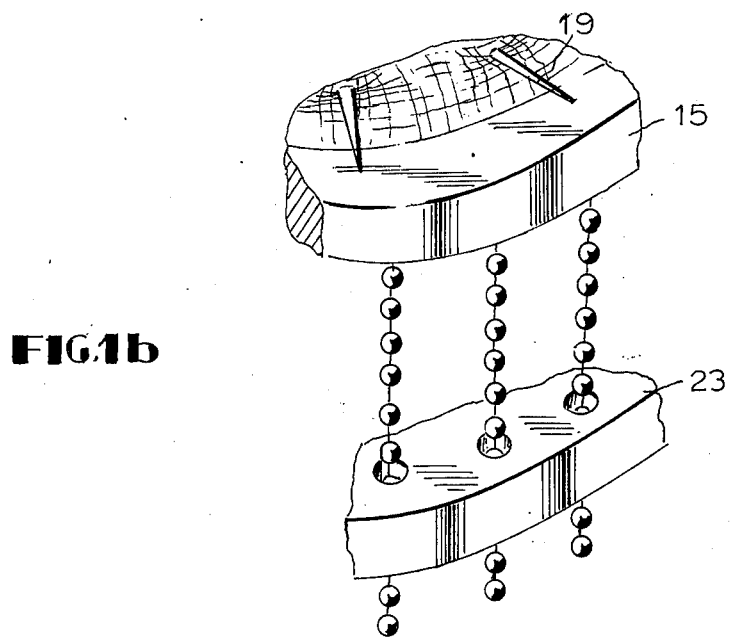
FIG. 1b represents a pictorial view of the apparatus showing the outward movement of needles against specimen resulting from separating the upper and lower plates.

FIG. 1b shows the circular embodiment of the pulleys with chain plate 23 separated from pulley plate 15 rotationally displacing each pulley unit and integral needle 19 outbound by an equal amount thus producing planar stretch in the attached grided specimen having a strain ratio of unity.

FIG. 1c depicts an intermediate orientation of the elements described in FIG. 1a showing the angular unit with a typical residual rotation of a pulley 16 element (FIG. 1c) after stretching an inelastic specimen and showing the plates at a gage separation in which the plates are slightly separated from their fully closed spacing. The fully closed spacing is known as the specimen loading position as in FIG. 1a.

The flats 18 integral pulley 16 of FIG. 1c serve as a driven cam to return the pulleys 16 to their initial angular orientation as the plates are restored to the specimen loading separation as in FIG. 1a. While approaching this fully closed position, the elasticity of a specimen is usually sufficient to return the pulley 16 to a position after which the base plate 23 contacts the outboard cam edge 28 of the flat 18 thereby rotating pulley 16 until inboard edge 29 of flat 18 stops in plane of plate 23 at a minimum plate separation, FIG. 1a.

When highly stretchable specimens are mounted in a manuallly-induced prestretched slate, plate 21 of FIG. 1a and FIG. 1c limits the inboard displacement of needles 19 (toward the center of the tester) as the plates are separated during subsequent testing. This said limit prevents the specimen from pulling itself off the needles. Chain slacks, given by the length of chain between clip 24 and plate 23 of FIG. 1a can also be adjusted to limit inboard needle displacement (pulley rotation) when manually prestretched specimens are tested. In addition, chain slack can also be varied between adjacent pulleys to produce a machine-imparted initial prestrain state in the specimen having a selected biaxial strain ratio due to unequal displacement of needles, subsequently followed by equal rotation of all pulleys when no chain slack remains. For normal testing, chain slack is kept at a small constant length per pulley with respect to having plate 23 at a gage separation as in FIG. 1c and with respect to having pulley 16 oriented in their initial rotational orientation as in FIG. 1a.

This gage position to which the conventional tensile testing machine (not shown) returns the crosshead 12, is normally set so that no indexing action occurs during testing. Indexing action on the pulley element takes place when the crosshead and integral plate 23 is moved from gage separation toward loading position as in FIG. 1a.

The supporting yoke 14 of FIG. 1a has sufficient clearance above the needle points so that specimens may be mounted without removing the yoke.

Needles 19 FIG. 1a are set toward center of plate 16 in order to increase the range of strain for which the total specimen remains in one plane.

In tests to measure elastic recovery, the magnitude of residual force on a needle against which the specimen must recover is controlled by the torque balance in the pulley, when oriented as in FIG. 1c. This external force is normally zero due to balance hole 27 but can be varied by e.g., the addition of weight to the chain below the clip.

In operation, the inventive device as exemplified by FIG. 1b is fixed onto the crosshead 12 and load cell coupling 13 of the conventional tensile testing machine not shown.

The crosshead 12 is positioned as in FIG. 1a thereby rigidly orienting needles all perpendicular to one plane for specimen mounting. A circular specimen larger than the circle formed by the needles is sandwiched between a smooth spatula and a rigid foamed board. The spatula is centered on top of the circle of needles, then the spatula is removed while holding the foamed board in place. The board is used to press the specimen onto the needles. The board is removed leaving the specimen 20 mounted and supported flatly by 21.

The plate 23 is manually separated to a gage position between the fully closed plate position FIG. 1a and the plate 23 displacement at which chain slack is minimal. In a test, the chain plate 23 is driven down away from gage, further separating plate 23 from 15 along a common plate axis. After all chain slack is taken up, a displacement in the chain plate 23 displaces each pulley-needle intersection point an equal length distance away from the midpoint of the specimen while the specimen remains on the perimeter of the rotated pulley.

The radial reaction force at each needle grip point resulting from the needle stretching the specimen is redirected around the pulley perpendicular to the plate 15 and is transmitted cumulatively to the pulley plate 15 integral load cell coupling 13 through the vertical reaction force at the pulley axle. A trim record of the plate 23 displacement and cumulative force is made by the conventional tensile testing machine (not shown).

After stretching to some desired stretch or force value as in FIG. 1b, the crosshead is returned to gage separation FIG. 1c, then manually returned to the specimen loading position, FIG. 1a. In this latter procedure, the specimen elasticity suffices to restore the pulley to a position for which the indexing elements 28 and 23 are operative. The returning plate 23, FIG. 1c, firstly contacts the edge 28 of flat 18 and pulley 16, said edge outboard pulley axle thus rotating pulley as a driven cam until inboard edge 29 lies in plate 23 stopping further rotation. For cyclic elastic recovery tests, the specimen remains on needles, while resting on smooth plate 21 FIG. 1c under a relaxed force condition.

Figure 2:
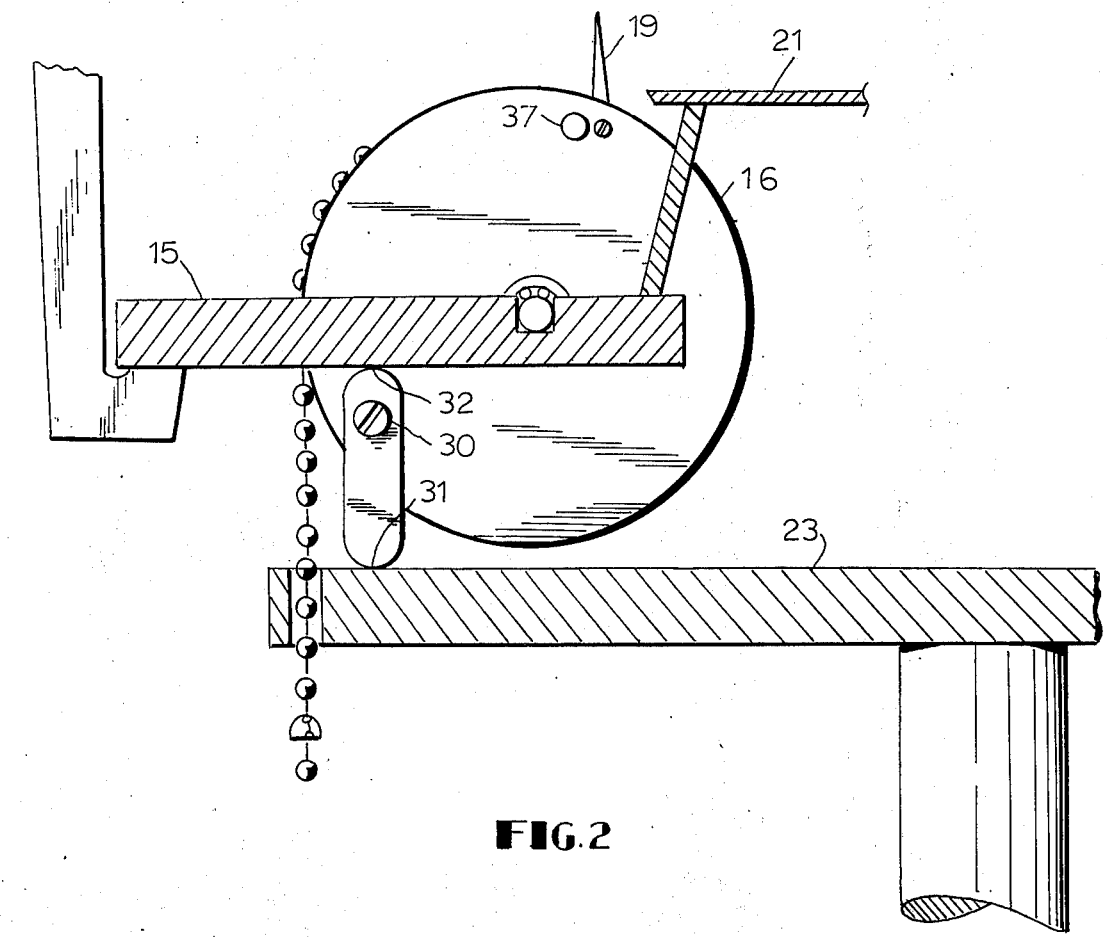
FIG. 2 is a schematic showing a second embodiment of a pulley element.

A second embodiment (FIG. 2) of pulley element having indexing and stop means comprises a spacer bar 30 fastened to pulley 16 said pulley may have material removed for balancing and adapted such that a cam surface 31 of said spacer contacts approaching plate 23 and rotates pulley 16 urging needle 19 inboard, said cam operative within vicinity of gage (not shown) and fully closed plate (FIG. 2) position, and adapted such that stop edge 32 contacts pulley plate 15 stopping inboard rotation, thus rigidly orienting integral needle 19 perpendicular to plate 15. A bar protrusion 33 on pulley 16 is a safety device positioned in order to contact plate 15 and prevent damage to needles 19 at maximum outboard displacement.

Other pulley indexing and stop means and variations and combinations thereof may be successfully utilized, for example the type of needle stop function attributed to specimen support plate element may be performed by a bar protrusion from the plane of the pulley situated to stop against pulley plate to limit the inboard displacement of needle, and will be obvious to those skilled in the art. An advantage in this apparatus is that small simple-shaped samples can be used in biaxial tests because common nonexpanding jaw-edge effects are eliminated.

The locus of specimen holding points given by the intersection of the needles with the plane of the specimen, approximating a continuous circular jaw, expands in perimeter as each point (needle) is displaced a specific amount radially away from the center of the specimen thus producing, in effect, an expandable circular jaw or clamp. A larger number of points will more closely approximate a continuous clamp, thus reducing edge effects. The strain between any two points is equal, thus the strain at any point in the circle is uniform in magnitude in all directions in the plane of the specimen.

For some purposes, the results of stretching textiles biaxially at fixed strain ratios other than unity, is desired. Parts of the apparatus of the embodiment disclosed can be arranged in a specific manner to stretch a specimen to produce a different uniform state of strain in the plane of the specimen having a strain ratio other than unity along with the other advantages attributable to the disclosed embodiment. The pulleys can be arranged on an elllipse in order to produce a specific, uniform state of strain in the surface of the specimen, that is, having a specific strain ratio as well as uniform magnitudes of directional strain at all points within the specimen for any plate separation--this is a general description of uniform planar strain. In order to construct an apparatus to produce a mode of strain having a strain ratio of $a/b$ or $b/a$ pulley midpoints are placed at cartesian coordinate points $(x_i, y_i)$ on the ellipse given by:

$$\frac{x^2}{A} + \frac{y^2}{B} - 1 = 0$$

inscribed in the plane of a pulley plate.

$A = C \cdot a$ and $B = C \cdot b$ are the magnitudes of the principal axes of the ellipse. The central plane of the pulleys are oriented perpendicular to the plate and at angles $\theta_i$ with respect to the $x$ axis where $\theta_1$ is the angle associated with the cartesian coordinates of the point $x_i, y_i$ through the parametric equations of the ellipse, namely $x_i = A \cos \theta_i$ and $y_i = B \sin \theta_i$. Note that the specific embodiment disclosed in the drawings is a special case of the general elliptic case in which the strain ratio is unity.

Although the instant invention is described in terms of pulleys each having the same chain pulley radius and specifically arranged on a specific ellipse for a given strain ratio, the successful operation of the instant invention is not so limited. The invention can also be accomplished by angularily positioning graduated pulleys at points around a circle. The pulleys are graduated by changing the chain pulley radius $R_j$ at which the chain drives the pinned-pulley while keeping the radius R upon which the specimen is stretched fixed. In addition, the pulleys are oriented at specific angles in planes perpendicular to the plane of the plate containing the circular array of pinned-pulleys. In order to construct a tester to produce a strain ratio of D/E, place pinned-pulley axle-centers at cartesian coordinate points $(X_j, Y_j)$ on a circle of radius R defined by equation $X_j^2 + Y_j^2 = R^2$ inscribed in the plane of the pulley plate. The central plane of the $j^{th}$ pinned pulley is oriented perpendicular to the plate at an angle $\theta_j$ (with the X axis) where $\theta_j = \tan^{-1} (D/E \cdot \alpha_j)$, and where $\alpha_j$ is the angle subtended by a radius of the circle to the point $(X_j, Y_j)$, and given by $\alpha_j = \tan^{-1} (X_j/X_j)$. The radius of the pulley for the chain of the $j^{th}$ pinned pulley will be given by $$R_j = \frac{R_o[(D \sin \alpha_o)^2 + (E \cos \alpha_o)^2]^{1/2}}{[(D \sin \alpha_j)^2 + (E \cos \alpha_j)^2]^{1/2}}.$$

$R_0$ is the value of the chain drive pulley radius having the largest value and $\alpha_o$ is the angular position of the axle center of the zero$^{th}$ pulley having chain pulley radius $R_0$. Note that the apparatus of the invention disclosed is a special case of this generalized "angled and graduated pulley" case in which the strain ratio D/E equals unity.

I claim:

1. A device for imparting a uniform state of strain to a textile comprising in combination:

A first generally disk-shaped plate carrying a plurality of pulleys, each pulley holding an integral needle, means associated with first said plate for supporting a portion of a specimen encircled by the array of needles, a second generally disk-shaped plate, means associated with said second plate and pulley to provide controlled movement and indexing of the pulleys of said first plate, and means for supporting said first plate, said second plate, said supporting means adapted for attachment to external means for separating said plates, in the form of a tensile-testing machine, said first generally disk-shaped plate, carrying a plurality of rotatable, radially mounted, generally disk-shaped pulleys spaced symmetrically relative to its adjacent counterpart pulleys, perpendicular to plane of first said plate, each pulley, when oriented in sample loading position, holding a needle (for gripping the specimen) mounted in a plane parallel to the plane of the pulley on a line generally parallel to a radius of the pulley, said pulley radius perpendicular to said first plate, with the extending point of said needle directed away from said first and said second plate, a specimen support means comprising a generally disk shaped surface parallel to first said plate said surface supporting portion of specimen encircled by needles during relaxation of forces on needles, said surface situated generally level with plane formed by the intersection of the pulley periphery and integral needles when said elements of the apparatus are in the specimen loading position said support means not contacting specimen during stretching of the specimen, driving means for each pulley comprising a chain, one end of which is removably mounted to pulley adjacent base of said needle, said chin lying along periphery of said pulley, said chain proceeding outboard around pulley through said first plate through said second generally disk-shaped plate, said second plate having a plurality of holes equal in number to number of chains, said holes of sufficient diameter to pass chain with clearance, chain length-dictating stop means associated with chain and said second plate to define minimum positive separation of said first and said second plates at which pulley rotation is initiated, support means for said second plate adapted to attach to external means in the form of a crosshead of a tensile-testing machine, and indexing means associated with each pulley, said indexing means adapted to rotationally establish said pulley in the specimen loading position.

* * * * *